United States Patent [19]
Sayama

[11] Patent Number: 5,439,823
[45] Date of Patent: Aug. 8, 1995

[54] APPARATUS FOR FAST FERMENTATION TREATMENT

[75] Inventor: Takashi Sayama, Sakai, Japan

[73] Assignee: Martial Plant Corporation, Osaka, Japan

[21] Appl. No.: 202,231

[22] Filed: Feb. 25, 1994

[30] Foreign Application Priority Data

Sep. 1, 1993 [JP] Japan .................... 5-217327

[51] Int. Cl.⁶ .................... A01C 3/02; C12M 1/02; C12M 1/06; C12M 1/38
[52] U.S. Cl. .................... 435/290; 210/150; 422/200; 435/286; 435/315
[58] Field of Search ............ 210/150, 151; 422/200, 422/201; 435/262.5, 268, 290, 306, 286, 315, 316

[56] References Cited

U.S. PATENT DOCUMENTS

| | | | |
|---|---|---|---|
| 670,520 | 3/1901 | Stitzel | 435/306 |
| 3,925,165 | 12/1975 | Muller | 435/316 |
| 4,100,023 | 7/1978 | McDonald | 435/316 |
| 4,238,337 | 12/1980 | Peters et al. | 435/316 |
| 5,102,803 | 4/1992 | Weaver | 435/315 |
| 5,258,306 | 11/1993 | Goldfarb | 435/315 |

FOREIGN PATENT DOCUMENTS

| | | | |
|---|---|---|---|
| 3525455 | 1/1987 | Germany | 435/290 |
| 232290 | 10/1986 | Japan | 435/316 |
| 338187 | 11/1992 | Japan | 435/316 |

*Primary Examiner*—Jeffrey E. Russel
*Attorney, Agent, or Firm*—Nixon & Vanderhye

[57] ABSTRACT

An apparatus for fast fermentation treatment rapidly increases the temperature of organic industrial waste to effect fast fermentation at a low running cost. Hot water is circulated inside a rotary shaft of a main body, and a sheath heater is provided on an exterior surface of the main body. Organic industrial waste and ferment bacilli are put into the main body which increases the temperature of the organic industrial waste to about 60° C. within one hour using the hot water inside the rotary shaft and the sheath heater. Subsequently, the sheath heater may be operated intermittently or deactivates because natural fermentation heat is generated from the organic industrial waste.

4 Claims, 2 Drawing Sheets

APPARATUS FOR FAST FERMENTATION TREATMENT

BACKGROUND OF THE INVENTION

1. Field of the Invention

The present invention relates to an apparatus for fast fermentation treatment which quickly ferments organic industrial waste or the like in an optimum condition.

2. Description of the Prior Art

There are daily produced unimaginably huge amounts of organic industrial wastes from the food processing industry, bean curd manufacturing industry, pharmaceutical industry, stock-raising industry, and fishing industry. These organic industrial wastes are currently dumped on reclaimed land or incinerated. However, the dumping and incineration of the wastes disadvantageously require considerable energy resulting in increased costs, and may cause secondary environmental pollution.

In view of the above-mentioned problems, it has been tried to treat the organic industrial wastes with a fermentation accelerating agent (ferment bacillus). However, due to the slowness of the fermentation, the above-mentioned method has not been put into practice.

SUMMARY OF THE INVENTION

An object of the present invention is therefore to provide an apparatus for fast fermentation treatment capable of producing fermented manure and fermented feed by rapidly fermenting organic industrial waste and the like.

In order to achieve the aforementioned object, the apparatus for fast fermentation treatment according to a first aspect of the present invention includes a main body which has an inlet and an outlet and receives therein organic material to be treated; a rotary shaft through which hot water circulates and which is rotatably provided in the main body with a paddle for stirring the organic material to be treated; a drive unit for driving the rotary shaft; an electric heater provided on an exterior surface of the main body; a temperature sensor for detecting temperature of the main body; a control section for controlling the electric heater so that the main body comes to have a specified temperature based on a signal representing the temperature of the main body from the temperature sensor; and a blower for discharging gas from the main body to supply air through an opening into the main body.

The apparatus for fast fermentation treatment according to a second aspect of the present invention is characterized in that a hot water jacket is provided on the exterior surface of the main body so that the jacket covers the electric heater.

The apparatus for fast fermentation treatment according to a third aspect of the present invention is characterized in that the main body is formed by connecting two containers each of which has an inlet and an outlet.

The apparatus for fast fermentation treatment according to a fourth aspect of the present invention is characterized in that the control section controls the electric heater so that the temperature of the material to be treated in the main body falls within a range of 55° C. to 70° C.

In the apparatus for fast fermentation treatment according to the first aspect of the present invention, an organic material to be treated is put into the main body from the inlet, and further a material containing a low moisture content such as rice bran and ashes is put into the main body to adjust the moisture content of the organic material to thereby achieve a total moisture content of 50 to 60%. Subsequently, a fermentation accelerating agent (ferment bacillus) is put into the main body from the inlet. Then hot water is supplied to the rotary shaft and the electric heater is turned on to raise a temperature of the organic material to a specified temperature. The temperature is one at which the ferment bacilli neither die nor sleep but are rather at full activity. Since the temperature control is performed by heating the exterior surface of the main body using the electric heater and by making hot water flow through the rotary shaft, the temperature of the organic material to be treated can be raised rapidly to the specified temperature. Particularly because the exterior surface of the main body which tends to be cooled is heated by the electric heater, the temperature control achieves a rapid rise in temperature. With the temperature thus controlled, the rotary shaft is rotated by the drive unit to stir the organic material to be treated, while the blower is driven to supply air through the opening into the main body to promote the activity of the ferment bacilli.

The organic material is evenly stirred inside the main body by the paddle to achieve an even temperature distribution and evenly put in contact with air to achieve a very active fermentation. When natural fermentation heat is generated after the passage of a specified time, sufficient to maintain the main body temperature at a specified temperature, the control section turns off the electric heater upon reception of a signal from the temperature sensor which detects the temperature. Subsequently, the organic material is heated mainly by the hot water inside the rotary shaft and the natural fermentation heat. Since the main body is not continually heated by the electric heater, a low running cost can be achieved.

The above-mentioned rotary shaft rotates forwardly, reversely, and intermittently with the intermission of a specified time. The aforementioned blower may be driven at intervals of a specified time by using a timer. The rotary shaft, electric heater, and the blower can be driven respectively by other appropriately selected methods instead of the above-exemplified method.

When the fermentation is thus completed, the organic material is dried into powdery fermented manure or fermented feed having a moisture content of 20% or lower. The above-mentioned products are discharged through the outlet.

According to the apparatus for fast fermentation treatment according to the second aspect of the present invention, the electric heater is covered with a hot water jacket, and therefore temperature control of the exterior surface of the main body is effected both by the hot water and the electric heater. Therefore, the apparatus has the advantage that the temperature control achieves a rapid temperature rise as well as the advantage that it can cope with a large-capacity container, which leads to a low running cost for the temperature control.

According to the apparatus for fast fermentation treatment according to the third aspect of the present invention, each of the two containers has an inlet and an outlet. In the case of an organic material of which fermentation can be completed in 48 hours, by operating the apparatus for fast fermentation treatment by putting an organic material into one container and organic material into the other container after the lapse of 24 hours, the organic material can be put into the apparatus for fast fermentation treatment continuously every day and the fermented manure and fermented feed can be taken out every day.

According to the apparatus for fast fermentation treatment according to the fourth aspect of the present invention, the electric heater is controlled by the control section so that the organic material has a temperature of 55° C. to 70° C. Therefore, the ferment bacilli are put in a condition where they are in full activity, which leads to fast fermentation.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

An embodiment of the present invention will now be described in detail with reference to the attached drawings.

Figure 1:
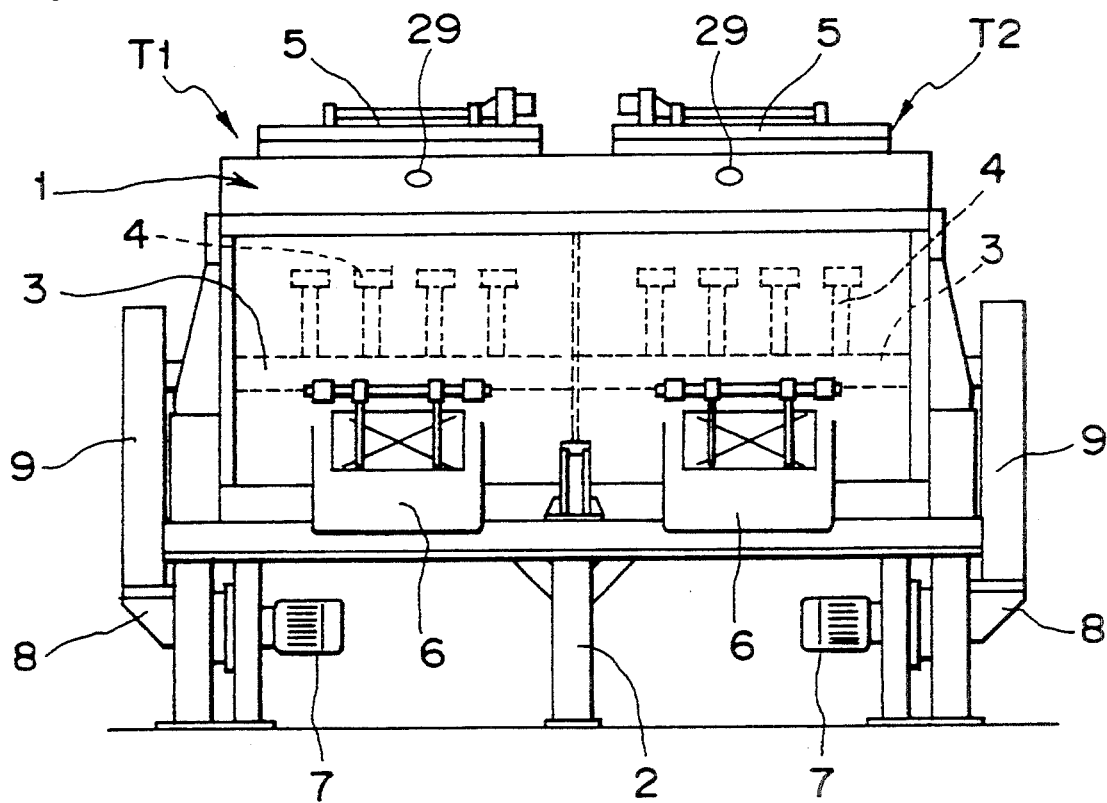
FIG. 1 is a front view of an apparatus for fast fermentation treatment in accordance with an embodiment of the present invention.
Figure 2:
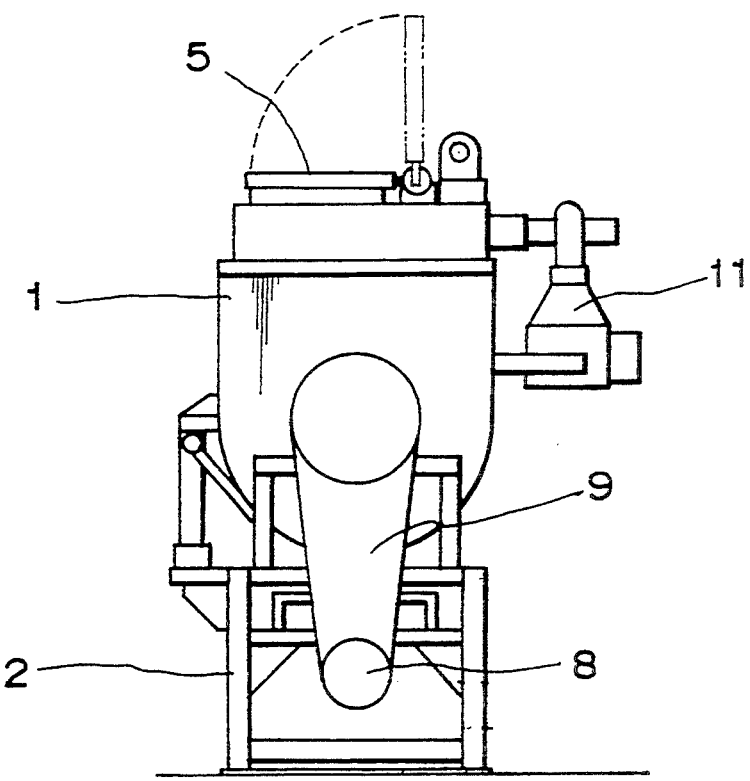
FIG. 2 is a side view of the embodiment shown in FIG. 1.

FIGS. 1 and 2 are front and side views of an apparatus for fast fermentation treatment respectively. A main body 1 is formed by connecting a first container T1 with a second container T2 and is supported by a leg 2. The main body 1 has a half-oval section shape. A rotary shaft 3 through which hot water circulates has a paddle 4 inclined at an angle of 30° to 34° with respect to a plane perpendicular to the axis of the rotary shaft and is rotatably supported by the main body 1. The first container T1 and the second container T2 are provided with inlets 5 at upper portions, and are provided with outlets 6 at lower portions respectively. The apparatus is further provided with a motor 7 which serves as a drive unit for driving the rotary shaft forwardly and reversely via a reduction gear 8 and a chain 9.

As shown in FIG. 2, a blower 11 is fixed to a side portion of the main body 1 to discharge the gas from the main body 1 and take air through an opening 29 as shown in FIG. 1 into the main body 1.

Figure 3:
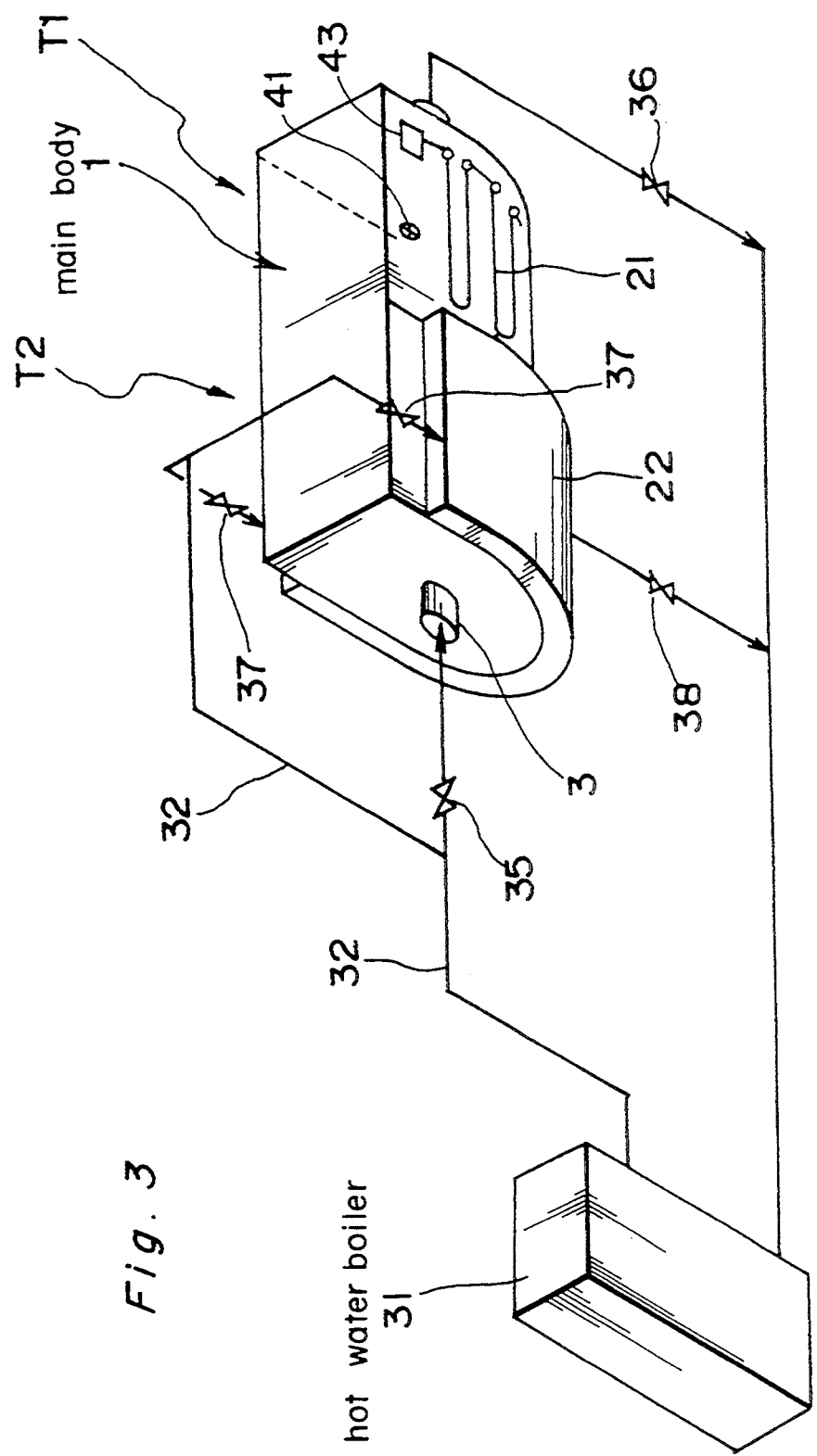
FIG. 3 is a schematic view of a heat source of the embodiment shown in FIG. 1.

FIG. 3 is a schematic view of a heat source of the apparatus for fast fermentation treatment as shown in FIG. 1. Hot water having a temperature of about 80° C. from a hot water boiler 31 passes through a pipe 32 and a valve 35 to be conducted into the rotary shaft 3 via a universal joint (not shown), and the hot water which has passed through the rotary shaft 3 returns to the hot water boiler via a valve 36.

Meanwhile, a sheath heater 21 is provided on the exterior surface of each of the aforementioned first container T1 and second container T2 (only the heater of the first container T1 is shown). There is further provided a thermistor 41 which serves as a temperature sensor on the surface of the main body 1. A signal representing the temperature output from the thermistor 41 is input to a control section 43 which controls the supply of electricity to the sheath heater 21 to keep the surface temperature of the main body 1 at 60° C. to 80° C.

There is further provided a U-shaped hot water jacket 22 around the aforementioned first container T1 and the second container T2 so that the jacket covers the sheath heater 21 (only the jacket of the second container T2 is shown). To an upper portion of the hot water jacket 22 is supplied hot water having a temperature of 80° C. through a pipe 32 and valves 37 and 37, and the hot water discharged from a lower portion of the hot water jacket 22 returns to the hot water boiler 31 via a valve 38.

The apparatus for fast fermentation treatment having the above-mentioned construction operates in a manner as follows.

First, pre-treatment is effected so that the moisture content of the organic material to be treated such as organic industrial waste is made to be 50% to 60%. Before putting the organic material into the main body 1, fishes, vegetables, meats and the like are pre-treated by means of a crusher, a screw press, or the like to adjust the moisture content to 50% to 60%. Meanwhile, the moisture content of bean-curd refuse, mud, and the like are adjusted to 50% to 60% by means of a dryer or a press. When no such pre-treatment equipment as above is used, rice bran, ashes, or the like is added to the organic material to be treated to adjust the moisture content to achieve a condition where the ferment bacilli are in full activity. Otherwise, fermented manure and fermented feed, i.e., treated products which already have undergone fermentation treatment are added as a moisture content adjuster to the organic material to be treated. The fermentation capability is three times greater when the pre-treatment is effected than when not.

Then the hot water having a temperature of 80° C. is supplied from the hot water boiler 31 into the rotary shaft 3, while the sheath heater 21 is turned on. The thermistor 41 detects the temperature of the main body and based on the detected temperature, the control section 43 controls the heater so that the temperature inside the first container is maintained between 60° C. and 80° C.

Then the organic material to be treated, having a moisture content adjusted to 50% to 60% in the pre-treatment stage, is put into the first container T1 from the inlet 5. Subsequently, the rotary shaft 3 is rotated in the forward direction for five minutes by motor 7 via the reduction gear 8 and the chain 9, stopped for one minute, and rotated in a reverse direction for five minutes. Further, the blower 11 is driven to discharge the gas from the first container T1 and to cause air to enter into the first container T1 through the opening 29 which further promotes the activity of the aerobic ferment bacilli.

With the above-mentioned operation, the organic material put in the container is stirred by the paddle 4 as the rotary shaft 3 rotates, and receives heat from the rotary shaft 3, sheath heater 21, and hot water jacket 22 to a temperature of 60° C. or higher in about one hour. Using the sheath heater 21, a temperature of 60° C. or higher can be achieved in a short time of about one hour. Subsequently, natural fermentation heat is generated by the organic material, and as a result, the temperature of the material rises to 60° C. or higher even when the sheath heater 21 is turned off. Therefore, the hot water inside the rotary shaft 3 and the hot water jacket 22 is only required for initial heating, which leads to a lower running cost.

When such an operation as described above is continued, even large lumps loose their shape in about 24 hours. The fermentation treatment completes in 48 hours, and dried powdery fermented product having a moisture content of 20% or less, i.e., fermented manure and fermented feed can be obtained. The fermented product is collected to a lower center portion of the main body 1 by reversely rotating the rotary shaft 3 and then taken out of the outlet 6.

After 24 hours from starting to drive the first container T1, the second container T2 starts to be driven in the same manner as the first container T1. Since the fermentation treatment is completed in 48 hours in the present embodiment, when the first container T1 and the second container T2 start to be driven with a time lag of 24 hours therebetween, the organic material to be treated can be put in the apparatus for fast fermentation treatment every day, and the resulting powdery fermented product, i.e., fermented manure and fermented feed, can be taken out of the apparatus for fast fermentation treatment every day. Thus the organic industrial waste can be continuously subject to the fast fermentation treatment and recycled into fermented manure and fermented feed. Furthermore, the sheath heater 21 operates only at the initial activation time when a rapid response is required, which also leads to a low running cost.

Although the main body is composed of the first container and the second container in the above-mentioned embodiment, the main body may be composed of only the first container. In another case, the electric heater may be only provided on the exterior surface of the main body without providing the hot water jacket.

As is evident from the above description, according to the apparatus for fast fermentation treatment according to the first aspect of the present invention, temperature of material to be treated inside a main body is controlled to a constant temperature by means of hot water circulating through a rotary shaft provided with a paddle and an electric heater provided on the exterior surface of the main body. Therefore, the temperature of the organic material to be treated can be rapidly increased in the start-up stage by operating the electric heater. In the time of a steady-state operation, the organic material can be maintained at a temperature at which optimum fermentation is achieved merely by adding hot water to the organic material utilizing the natural fermentation heat even when the electric heater is turned off or intermittently operated, which leads to a low running cost. Furthermore, since gas generated inside the main body is exhausted and air is drawn into the main body through the opening, the activity of the aerobic bacilli can be promoted.

According to the apparatus for fast fermentation treatment according to the second aspect of the present invention, the electric heater is covered with a hot water jacket, and therefore the temperature of the exterior surface of the main body which tends to be cooled easily is controlled by the hot water and the electric heater. Therefore, the apparatus for fast fermentation treatment according to the second aspect of the present invention has the advantage that the temperature control achieves a rapid rise in temperature as well as the advantage that it can cope with a large-capacity container, which leads to a low running cost for the temperature control.

According to the apparatus for fast fermentation treatment according to the third aspect of the present invention, each of two containers has an inlet and an outlet. Therefore, in the case of an organic material of which fermentation can be completed in 48 hours, organic material to be treated is put into one container and another organic material to be treated is put into the other container after the lapse of 24 hours. In this way, the organic material to be treated can be put into the apparatus for fast fermentation treatment continuously every day and the fermented manure and fermented feed can be taken out every day.

According to the apparatus for fast fermentation treatment according to the fourth aspect of the present invention, the electric heater is controlled by a control section so that an organic material to be treated has a temperature of 55° C. to 70° C. Therefore, the ferment bacilli are put in a condition where they are in full activity, which allows fermentation to be achieved fast.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An apparatus for fast fermentation treatment comprising:
   a main body having an inlet and an outlet for receiving organic material to be treated;
   a rotary shaft through which hot water circulates and which is rotatably provided in the main body with a paddle for stirring the organic material to be treated;
   a drive unit for driving the rotary shaft;
   an electric heater provided on an exterior surface of the main body;
   a temperature sensor for detecting temperature of the main body;
   a control section for controlling the electric heater so that the main body obtains a specified temperature based on a signal representing the temperature of the main body from the temperature sensor; and
   a blower for discharging gas from the main body to supply air through an opening in the main body.

2. An apparatus for fast fermentation treatment as claimed in claim 1, wherein a hot water jacket is provided on the exterior surface of the main body so that the hot water jacket covers the electric heater.

3. An apparatus for fast fermentation treatment as claimed in claim 1, wherein the main body includes two containers each of which has an inlet and an outlet.

4. An apparatus for fast fermentation treatment as claimed in claim 2, wherein the main body includes two containers each of which has an inlet and an outlet.

\* \* \* \* \*